US009662022B2

(12) United States Patent
Kyal et al.

(10) Patent No.: US 9,662,022 B2
(45) Date of Patent: *May 30, 2017

(54) CONTINUOUS CARDIAC SIGNAL GENERATION FROM A VIDEO OF A SUBJECT BEING MONITORED FOR CARDIAC FUNCTION

(71) Applicant: Xerox Corporation, Norwalk, CT (US)

(72) Inventors: Survi Kyal, Rochester, NY (US); Lalit Keshav Mestha, Fairport, NY (US); Beilei Xu, Penfield, NY (US)

(73) Assignee: Xerox Corporation, Norwalk, CT (US)

( * ) Notice: Subject to any disclaimer, the term of this patent is extended or adjusted under 35 U.S.C. 154(b) by 424 days.

This patent is subject to a terminal disclaimer.

(21) Appl. No.: 13/871,766

(22) Filed: Apr. 26, 2013

(65) Prior Publication Data

US 2014/0323888 A1    Oct. 30, 2014

(51) Int. Cl.
   *A61B 5/024*    (2006.01)
   *A61B 5/00*    (2006.01)
   *A61B 5/021*    (2006.01)
   *A61B 5/0295*    (2006.01)

(52) U.S. Cl.
   CPC .......... *A61B 5/02405* (2013.01); *A61B 5/021* (2013.01); *A61B 5/0295* (2013.01); *A61B 5/02416* (2013.01); *A61B 5/02444* (2013.01); *A61B 5/7225* (2013.01)

(58) Field of Classification Search
   CPC ... A61B 5/0033; A61B 2576/00; A61B 5/021; A61B 5/024; A61B 5/02416; A61B 5/0295; G06T 7/0012

USPC ........................................................ 600/508
   See application file for complete search history.

(56) References Cited

U.S. PATENT DOCUMENTS 8,855,384 B2 * 10/2014 Kyal .................... G06K 9/0057
                                                                                            382/107

OTHER PUBLICATIONS

Poh et al. Non-contact. automated cardiac pulse measurements using video imaging and blind source separation. Optics Express 18 (2010): 10762. © 2011 Optical Society of America.*

(Continued)

*Primary Examiner* — Christopher D Koharski
*Assistant Examiner* — Jeremiah Kimball
(74) *Attorney, Agent, or Firm* — Philip E. Blair; Fleit Gibbons Gutman Bongini & Bianco P.L.

(57) ABSTRACT

What is disclosed is a system and method for extracting photoplethysmographic (PPG) signal (i.e., a cardiac signal) on a continuous basis from a time-series signals obtained from video images captured of a subject being monitored for cardiac function in a non-contact remote sensing environment involves the following. First, a time-series signal obtained from video images captured of a region of exposed skin where a photoplethysmographic (PPG) signal of a subject of interest can be registered. A sliding window is then used to define consecutive sequential segments of the time-series signal for processing. Each of the consecutive time-series signal segments is detrended such that low frequency variations and non-stationary components are removed. The detrended signals are processed to obtain, for each segment, a PPG signal. The PPG signal segments are then stitched together using a stitching method, as disclosed herein, to obtain a continuous PPG signal for the subject.

8 Claims, 8 Drawing Sheets

(56) References Cited

OTHER PUBLICATIONS

Tarvainen et al. An advanced detrending method with application to HRV analysis. IEEE Trans. Biomed. Eng., vol. 49, No. 2, pp. 172-175 (2002).*

Sun et al. Motion-compensated noncontact imaging photoplethysmography to monitor cardiorespiratory status during exercise. J. Biomed. Opt. 16(7), 077010 (Jul. 18, 2011).*

Poh et al. Advancements in Noncontact, Multiparameter Physiological Measurements Using a Webcam. IEEE Trans Biomed Eng Jan. 14, 2011;58(1):7-11.*

W. Gersch. Smoothness priors. New Directions in Time Series Analysis, Part II, pp. 113-146, Springer-Verlag, 1991.*

Kyal et al., "Continuous Cardiac Pulse Rate Estimation From Multi-Channel Source Video Data", U.S. Appl. No. 13/528,307, filed Jun. 20, 2012.

Kyal et al., "Continuous Cardiac Pulse Rate Estimation From Multi-Channel Source Video Data With Mid-Point Stitching", U.S. Appl. No. 13/871,728, filed Apr. 26, 2013.

* cited by examiner

CONTINUOUS CARDIAC SIGNAL GENERATION FROM A VIDEO OF A SUBJECT BEING MONITORED FOR CARDIAC FUNCTION

TECHNICAL FIELD

The present invention is directed to systems and methods for processing a time-series signal generated from video captured of a subject being monitored for cardiac function to obtain a continuous PPG signal from which beat-to-beat time intervals can be reliably extracted.

BACKGROUND

Monitoring cardiac events is of clinical importance in the early detection of potentially fatal conditions such as atrial fibrillation (AF or A-fib). Current technologies involve contact sensors such as Holter monitors the individual must wear constantly for detecting A-fib episodes. Such a requirement can lead to patient discomfort, dependency, loss of dignity, and further may fail due to a variety of reasons including refusal to wear the monitoring device. In A-fib patients, the variability in beat-to-beat intervals can be large and can lead to many spectral components. Hence detecting rate can be inaccurate and is not going to help in detecting cardiac arrhythmia effectively.

Accordingly, what is needed in this art are increasingly sophisticated systems and methods for processing a time-series signal generated from video captured of a subject to obtain a continuous PPG signal from which beat-to-beat time intervals can be reliably extracted and viewed without disturbing the resting cardiac patient.

INCORPORATED REFERENCES

The following U.S. Patents, U.S. Patent Applications, and Publications are incorporated herein in their entirety by reference.

"Continuous Cardiac Pulse Rate Estimation From Multi-Channel Source Video Data", U.S. Pat. No. 8,855,384.

"Continuous Cardiac Pulse Rate Estimation From Multi-Channel Source Video Data With Mid-Point Stitching", U.S. Pat. No. 9,036,877.

BRIEF SUMMARY

What is disclosed is a novel system and method for processing a time-series signal generated from video captured of a subject being monitored for cardiac function to obtain a continuous PPG signal from which beat-to-beat time intervals can be reliably extracted. The teachings hereof provide an effective algorithm to detect the presence of cardiac arrhythmia such as atrial fibrillation (A-fib) without disturbing the resting cardiac patient.

In one embodiment, the present method for extracting a photoplethysmographic (PPG) signal (i.e., a cardiac signal) on a continuous basis from a time-series signal obtained from video images of a subject involves the following. A time-series signal obtained from video images captured of a region of exposed skin where a photoplethysmographic (PPG) signal of a subject of interest can be registered. A sliding window is then used to define consecutive sequential segments of the time-series signal for processing. Then, each of the consecutive time-series signal segments is detrended such that low frequency variations and non-stationary components are removed. A specific detrending algorithm is disclosed. The detrended signals are filtered, using a band pass filter, such that frequencies of the subject's cardiac beat are retained. The filtered time-series signal segment are upsampled to a preselected sampling frequency to increase a total number of data points such that an accuracy of peak-to-peak pulse point detection can be enhanced. The upsampled time-series signal segment are smoothed to produce a processed PPG signal. The processed PPG signal segments are stitched together to obtain a continuous PPG signal for the subject. The continuous PPG signal is analyzed for beat-to-beat intervals such that a cardiac arrhythmia for the subject can be detected.

Many features and advantages of the above-described method will become readily apparent from the following detailed description and accompanying drawings.

BRIEF DESCRIPTION OF THE DRAWINGS

The foregoing and other features and advantages of the subject matter disclosed herein will be made apparent from the following detailed description taken in conjunction with the accompanying drawings, in which.

DETAILED DESCRIPTION

What is disclosed is a system and method for processing a time-series signal generated from video captured of a subject to obtain a continuous PPG signal from which beat-to-beat time intervals can be reliably extracted and viewed without disturbing the resting cardiac patient.

Non-Limiting Definitions

A "subject of interest", as used herein, refers to an organism having a heart. Although the term "human", "person", or "patient" may be used throughout this text, it should be appreciated that the subject of interest may be something other than a human being such as, for instance, an animal. Use of "person" or "patient" is not to be viewed as limiting the appended claims strictly to humans.

A "video" is a time-varying sequence of images captured using a video camera capable of acquiring video data over multiple data acquisition channels. The video may also contain other components such as, audio, time reference signals, and the like.

A "time-series signal" refers to a time varying signal generated from images of the captured video. The time-series signal generated from the captured video images can be RGB signals, IR signals, a combination of RGB and IR signals, multi-spectral signals, or hyperspectral signals. Time-series signals may be generated in real-time from a streaming video as in the case of continuous patient monitoring.

"Receiving a time-series signal" is intended to be widely construed and means to retrieve, receive, capture with a video capture device, or otherwise obtain a time-series signal for processing in accordance with the teachings hereof. In various embodiments, the time-series signal is retrieved from a remote device such as a computer workstation over a wired or wireless network or obtained on a continuous basis from a video stream.

"Cardiac function" refers to the function of the heart and, to a large extent, to the cardio-vascular system. In most species, the heart comprises muscle which repeatedly contracts to pump blood throughout the vascular network. Cardiac function can be impacted by a variety of factors including age, stress, disease, overall health, and the like. Cardiac function can also be affected by environmental conditions such as altitude and pressure.

"Photoplethysmography" is the study of signals containing relative blood volume changes in the blood vessels close to the skin. A subject's photoplethysmographic (PPG) signal contains important information about the subject's cardiac function.

A "sliding window" refers to a window of size win_size that identifies successive segments of a time-series signal for processing in accordance with the teachings hereof. Each successive batch has at least a 95% overlap with a previous batch. The overlap must be significant enough to ensure consistency in signal recovery estimation.

Figure 1:
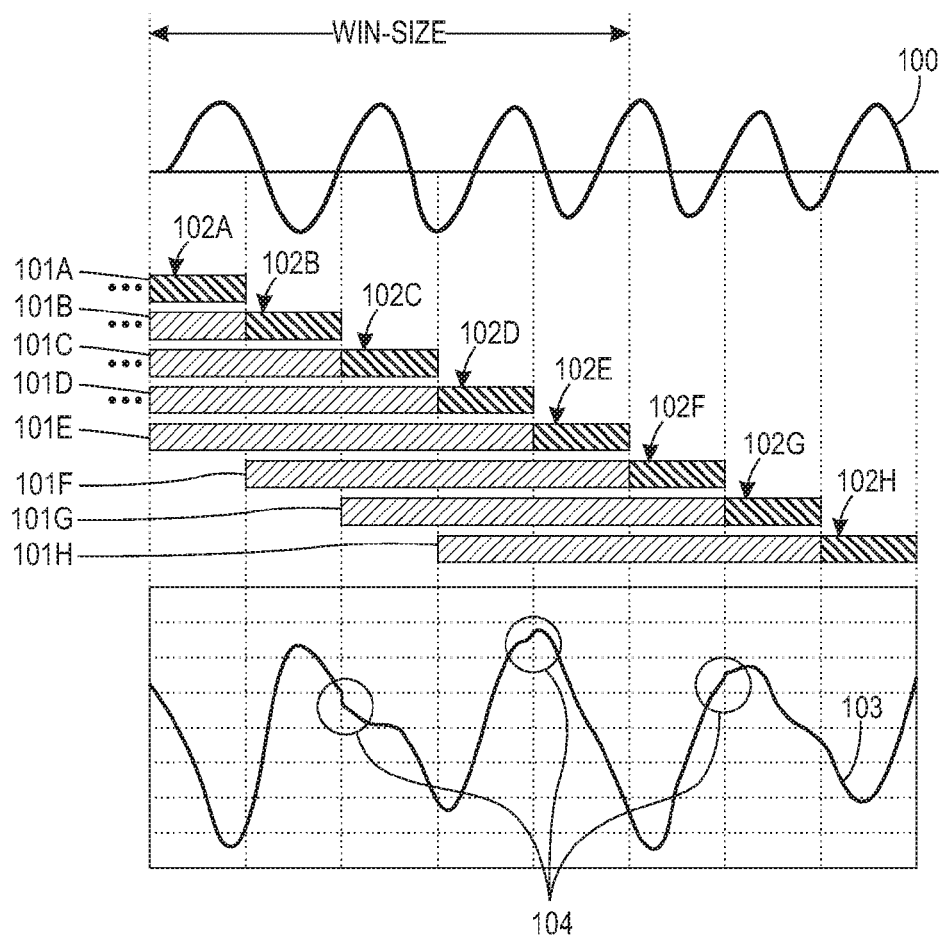
FIG. 1 illustrates a method of end-point stitching by which the processed PPG signal segments are stitched together to obtain a continuous PPG signal for the subject.

"Stitching via end-points" means of connecting end-points or end-sections of extracted PPG signals together to obtain a continuous cardiac signal for the subject of interest. Reference is now being made to FIG. 1 wherein a sliding window is used to process the time-series signal 100 into overlapping signal segments. Each time-series signal segment is processed according to the present method to generate a corresponding processed PPG signal segment 101A-H having a corresponding endpoint or end-section (at 102A-H). A continuous PPG signal 103 is obtained by "stitching" these end-sections together. End-point stitching may introduce artifacts, collectively at 104.

Figure 2:
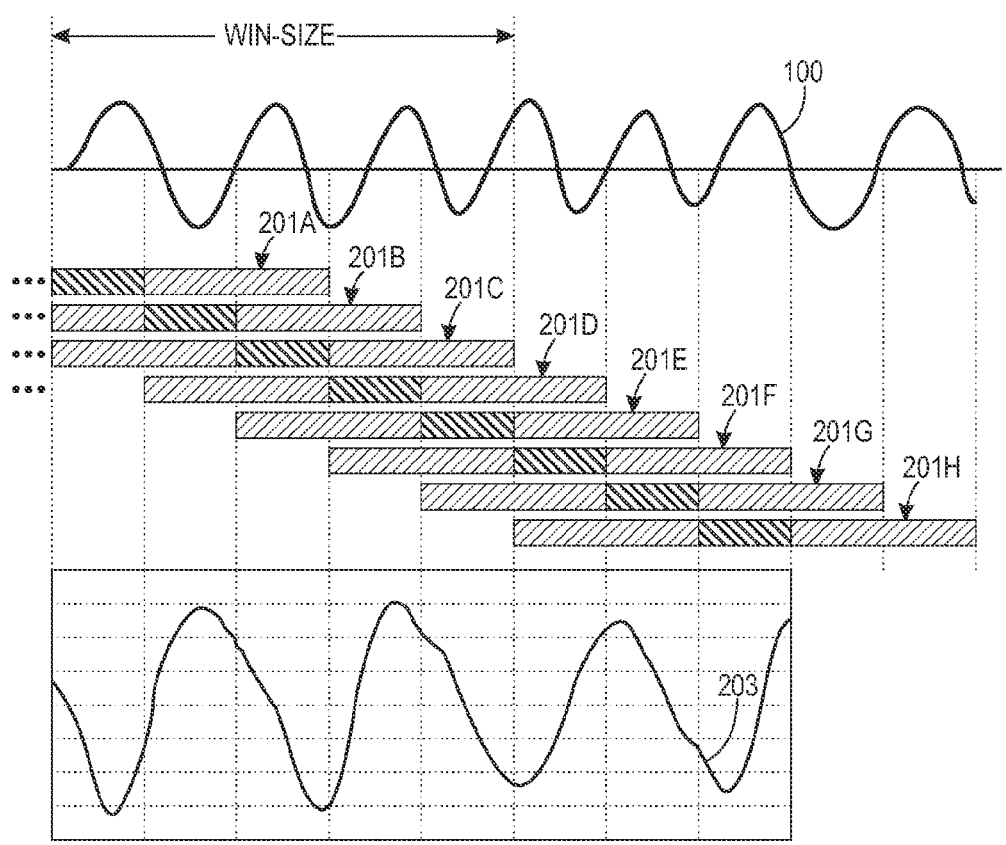
FIG. 2 illustrates a method of mid-point stitching by which the processed PPG signal segments are stitched together to obtain a continuous PPG signal for the subject.

"Stitching via mid-points" means connecting mid-sections of processed PPG signals together to obtain a continuous PPG signal. In FIG. 2, a sliding window is used to process the time-series signal 100 into overlapping signal segments. The time-series signal segments are processed in accordance with the teachings to obtain corresponding processed PPG signal segments 201A-H. A continuous cardiac signal 203 is generated by stitching the midpoints of each of the processed PPG signal segments together.

"Detrending" is a process of removing non-stationary trends and low frequency contents in a time-series signal segment. As used herein, the detrending algorithm is given by:

$$P_{stat} = (I - (I + \lambda^2 D_2^T D_2)^{-1}) P_{original}$$

where $P_{original}$ is a time-series signal segment of size N being processed, I is an identity matrix of size N×N, λ is used to adjust a frequency response of said algorithm, and $D_2$ is a second order difference matrix comprising:

$$D_2 = \begin{bmatrix} 1 & -2 & 1 & 0 & \ldots & \ldots & \ldots & 0 \\ 0 & 1 & -2 & 1 & \ldots & \ldots & \ldots & 0 \\ \ldots & \ldots & \ldots & \ldots & \ldots & \ldots & \ldots & 0 \\ \ldots & \ldots & \ldots & \ldots & \ldots & \ldots & \ldots & 0 \\ 0 & 0 & 0 & 0 & \ldots & 1 & -2 & 1 \end{bmatrix}.$$

"Filtering" is a technique which, in one embodiment, uses a band pass filter to retain desired frequencies such as, for instance, that of the subject's cardiac beat. One such filter is a higher order band limited Finite Impulse Response (FIR) filter which constrains the band width depending on the heart ranges of the subjects of interest.

"Upsampling" the filtered time-series signal segment to a preselected sampling frequency is a method of increasing a total number of data points such that an accuracy of peak-to-peak pulse point detection can be enhanced. In one embodiment, upsampling comprises interpolating the filtered time-series using, for instance, a cubic spline function with a pre-selected sampling frequency.

"Smoothing" is the upsampled time-series signal segment removes unwanted artifacts. In one embodiment, the smoothing algorithm is given by:

$$y(n) = \frac{1}{N} \sum_{1}^{N} x(n - i)$$

where N is the number of frames in a moving window of the video, x is an unfiltered PPG signal, y is a filtered PPG signal, n is a current frame, and i is an index designating a moving frame. It is to be noted that, number of frames N in the smoothing algorithm is unrelated to the number N used inside detrending algorithm. It should be understood that the smoothing, filtering, detrending, and upsampling steps are intended to be widely construed and not to be view as limiting the scope of the claims strictly to the embodiments described herein.

Example Video Acquisition System

Figure 3:
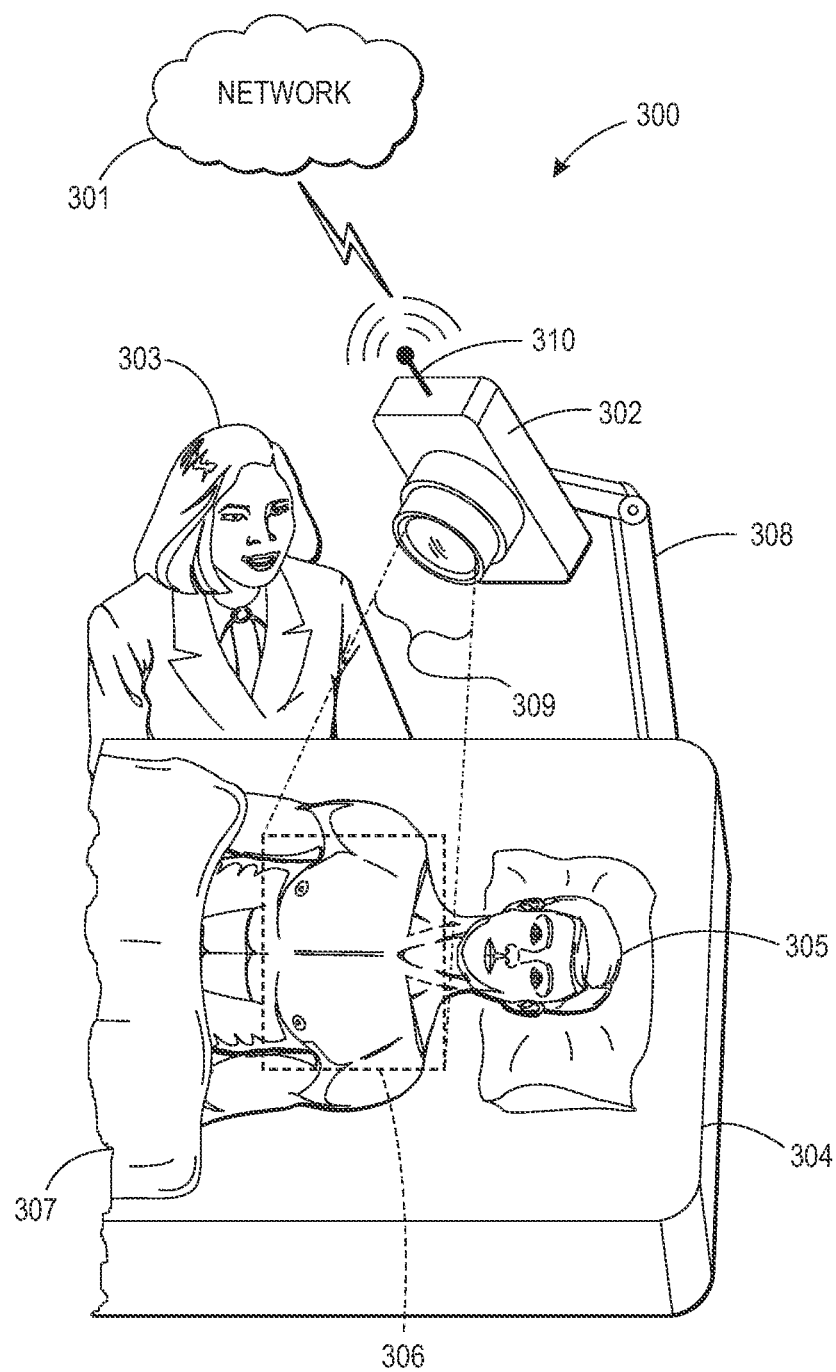
FIG. 3 illustrates an example system for capturing a video of a subject of interest.

Reference is now being made to FIG. 3 which illustrates an example video acquisition system for capturing a video of a subject of interest.

Examination room 300 has an example image capturing system 302 being operated by technician 303 standing at the bedside 304 of subject of interest 305 shown resting his/her head on a pillow while most of his body is partially covered by sheet 307. Camera system 302 is rotatably fixed to support arm 308 such that the camera's field of view 309 can be directed by nurse 303 onto an area of exposed skin of a chest area 306 of patient 305 for continuous monitoring of cardiac function. Support arm 308 is on a set of wheels so that the image capture system can be moved from bed to bed and room to room. Although patient 305 is shown in a prone position lying in a bed, it should be appreciated that images of the subject of interest being monitored for cardiac function can be captured while the subject is positioned in other supporting devices such as, for example, a chair or wheelchair, standing up, including walking or moving. The embodiment of FIG. 3 is not intended to be viewed as limiting the scope of the appended claims in any respect.

Camera system 302 captures video images of the subject of interest to be monitored for cardiac function. The captured video images comprises multi-channel source data such as RGB and/or multi-spectral acquired over time. Camera 302 comprises imaging sensors which may be a single sensor or a sensor array including a plurality of individual or separate sensor units. A central processor integral to camera 302 and in communication with a memory (not shown) and the imaging sensor may take a variety of forms each having the capability of detecting changes in the status of sensors and outputting an alarm, notice, report, and the like if a change in any hardware or software of the camera has been detected. Other sensors contemplated are capable of sensing a change of position or status of patient 305 and issue an alarm or notification via transmission element 310 to a nurse, doctor, or technician in the event that the cardiac function of the patient falls outside a set of pre-defined parameters. Antenna 310 is used to communicate the captured images to various remote devices. Transmitter 310 may be a wired (e.g., Ethernet) connection utilizing an Ethernet network consisting of Ethernet cables and an Ethernet hub that is in communication with a network 301.

Camera system 302 may include both wireless and wired elements and may be connected via other means such as coaxial cable, radio frequency, Bluetooth, or any other manner for communicating data. Network 301 receives time-series signals and communicates those signals to other devices such as, for instance, a workstation with a graphical display device, or a handheld device such as an iPhone, iPad, notebook, and the like. Techniques for placing devices in networked communication are well established. Therefore, a further discussion as to specific techniques for networking devices has been omitted. Any of the networked devices may include a network interface card or system.

Flow Diagram of One Embodiment

Figure 4:
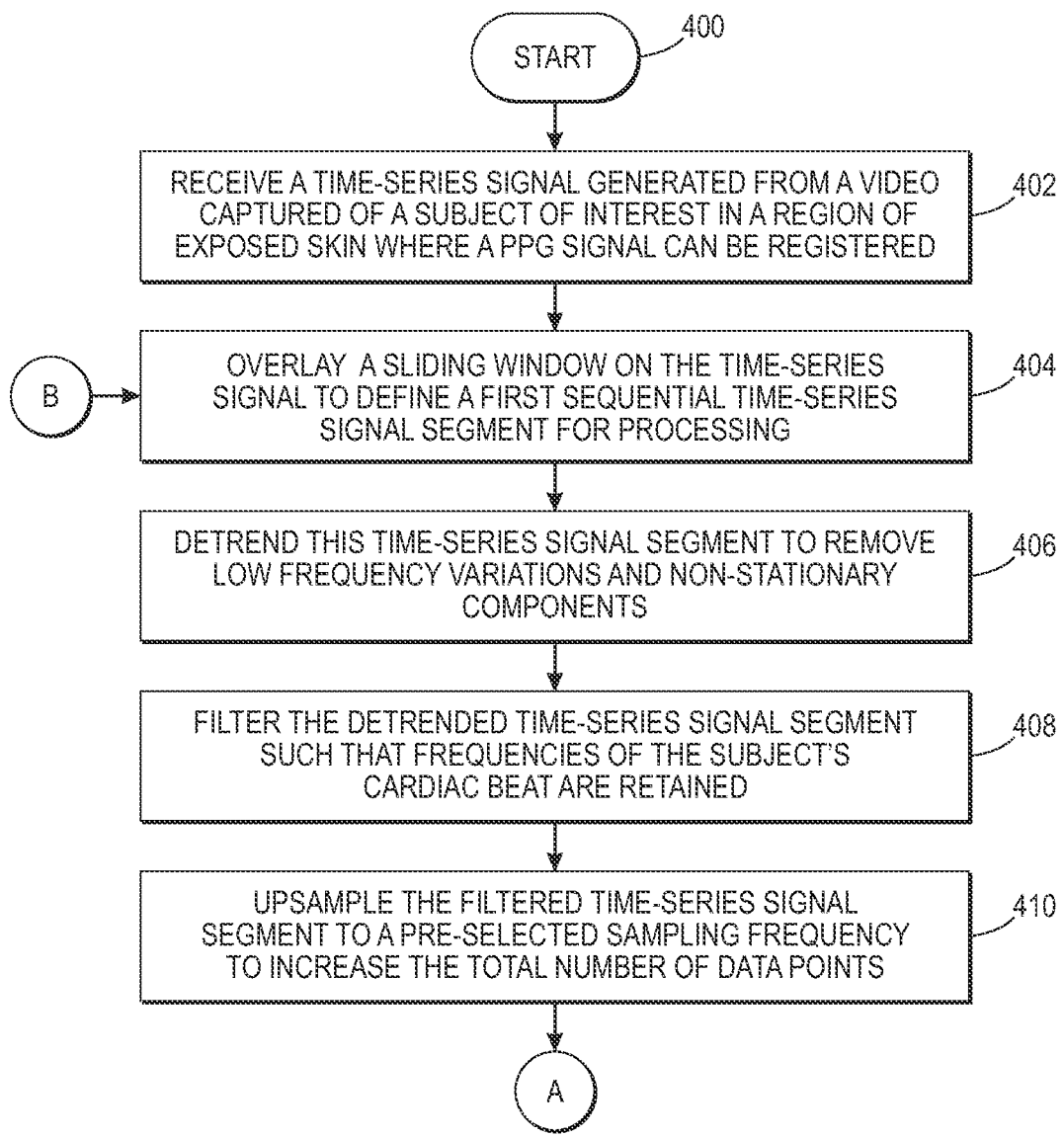
FIG. 4 is a flow diagram which illustrates one embodiment of the present method for extracting photoplethysmographic (PPG) signal (i.e., a cardiac signal) on a continuous basis from a time-series signal obtained from video images captured of a subject being monitored for cardiac function in a non-contact remote sensing environment.

Reference is now being made to the flow diagram of FIG. 4 which illustrates one embodiment of the present method for extracting photoplethysmographic (PPG) signal (i.e., a cardiac signal) on a continuous basis from a time-series signals obtained from video images captured of a subject being monitored for cardiac function in a non-contact remote sensing environment. Flow processing starts at step 400 and immediately proceeds to step 402.

At step 402, receive a time-series signal generated from video captured of a subject of interest in a region of exposed skin where a PPG signal can be registered. The time-series signal is obtained from having identified a region of interest such as, an area of exposed skin where a PPG signal can be detected. Video frames are spatially averaged over all pixels per frame to obtain the time-series signal. The time-series signal can be obtained from the video on a continuous basis. Alternatively, the video is capture and stored for subsequent processing.

At step 404, overlay a sliding window on the time-series signal to define a first sequential time-series signal segment for processing. There is at least a 95% overlap between consecutive batches of signal segments for processing. For example, if each signal segment is 30 seconds in length, each successive segment contains only 1 second of new data while 29 seconds of data from the previous batch is retained. The window length and the overlap length are resizable depending on the rate of change of the subject's cardiac pulse. The overlap in data frames should be significant enough to ensure consistency in signal recovery estimation. This will depend, to a large extent, on the time-series signals being processed and may be determined by trial and error or based upon past experience in processing such signals. Once a time-series signal segment has been identified, processing continues as follows.

At step 406, detrend this time-series signal segment to remove low frequency variations and non-stationary components. An embodiment of a detrending algorithm is provided herein.

At step 408, filter the detrended time-series signal segment such that frequencies of the subject's cardiac beat are retained.

At step 410, up-sample the filtered time-series signal segment to a preselected sampling frequency to increase the total number of data points. A larger number of data points comprising the filtered time-series signal effectively enhances the accuracy of peak-to-peak pulse point detection.

Figure 5:
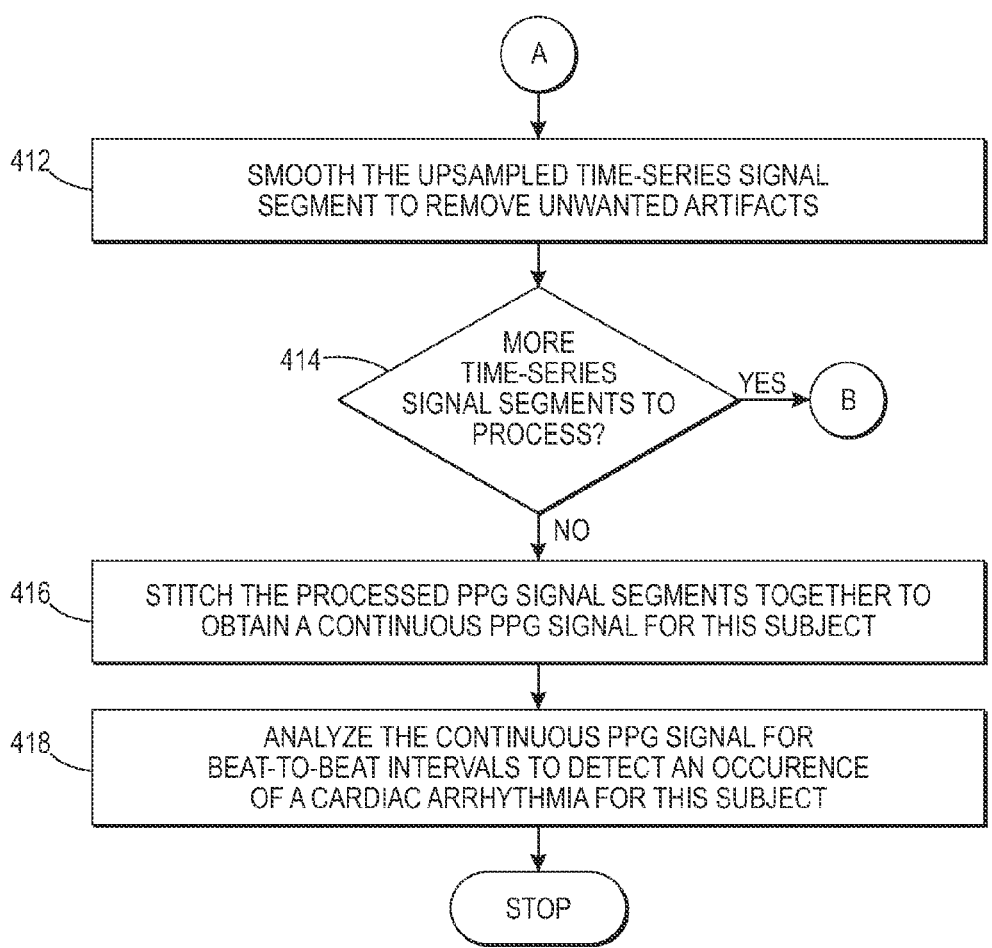
FIG. 5 is a continuation of the flow diagram of FIG. 4 with flow processing continuing with respect to node A.

Reference is now being made to the flow diagram of FIG. 5 which is a continuation of the flow diagram of FIG. 4 with flow processing continuing with respect to node A.

At step 412, smooth the upsampled time-series signal segment. An embodiment of a smoothing algorithm is provided herein. As a result of having performed steps 408-412, a processed PPG signal segment for the current time-series signal segment is obtained. The current processed PPG signal segment is communicated to a storage device or is retained in memory.

At step 414, a determination is made whether any more time-series signal segments remain to be processed. If so, then processing repeats with respect to step 404 wherein the sliding window is shifted to define a next time-series signal segment for processing. Processing for this next defined time-series signal segment repeats in a similar manner to obtain another processed PPG signal segment. Processing repeats until no more time-series signal segments remain to be processed.

At step 416, stitch the PPG signal segments together using a stitching method to obtain a continuous PPG signal. End-point stitching is shown and described with respect to FIG. 1. FIG. 2 illustrates a mid-point stitching technique.

At step 418, analyze the continuous PPG signal for beat-to-beat intervals to detect an occurrence of a cardiac arrhythmia for the subject. The continuous PPG signal can be communicated to a display device for viewing, in real-time, by a cardiac specialist. Thereafter, in this embodiment, further processing stops.

It should be appreciated that the flow diagrams hereof are illustrative. One or more of the operative steps illustrated in any of the flow diagrams may be performed in a differing order. Other operations, for example, may be added, modified, enhanced, condensed, integrated, or consolidated with the steps thereof. Such variations are intended to fall within the scope of the appended claims. All or portions of the flow diagrams may be implemented partially or fully in hardware in conjunction with machine executable instructions.

Example Sliding Window

Figure 6:
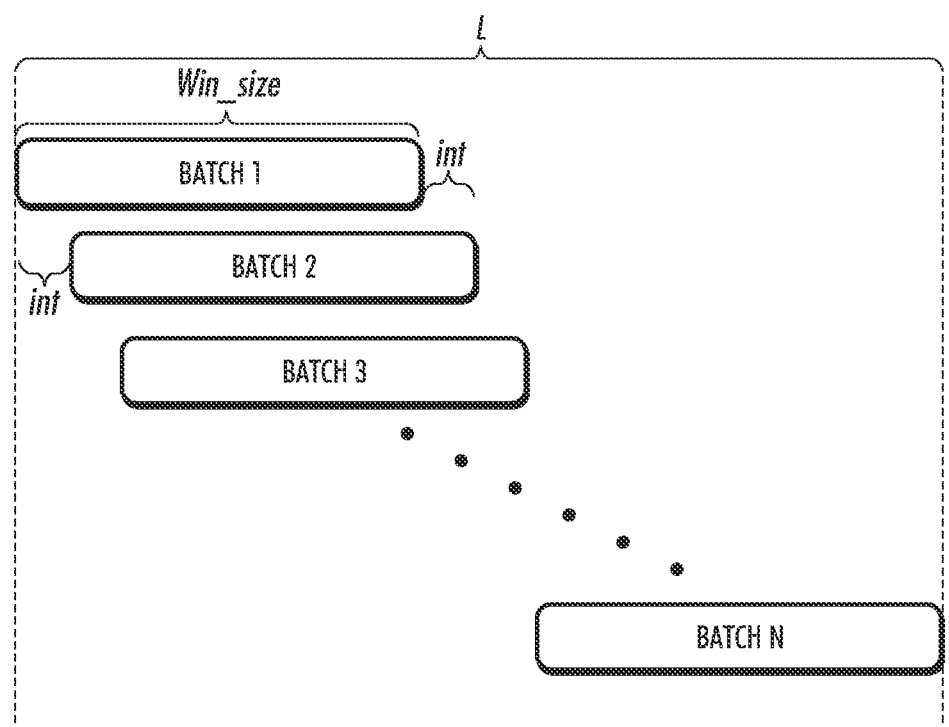
FIG. 6 illustrates a sliding window which is repeatedly shifted to define overlapping successive time-series signal segments for processing in accordance with various embodiments hereof.

Reference is now being made to FIG. 6 which illustrates a sliding window which is repeatedly shifted to define overlapping successive time-series signal segments for processing in accordance with various embodiments hereof. Video frames are spatially averaged over all pixels per frame to obtain RGB time varying signals or raw traces. For example, a sliding window defining 30 second segments of time-series signal for processing with 96% overlap between consecutive batches means each segment contains only 1 second of new data and retains 29 seconds of data from the previous batch.

Example Functional Block Diagram

Figure 7:
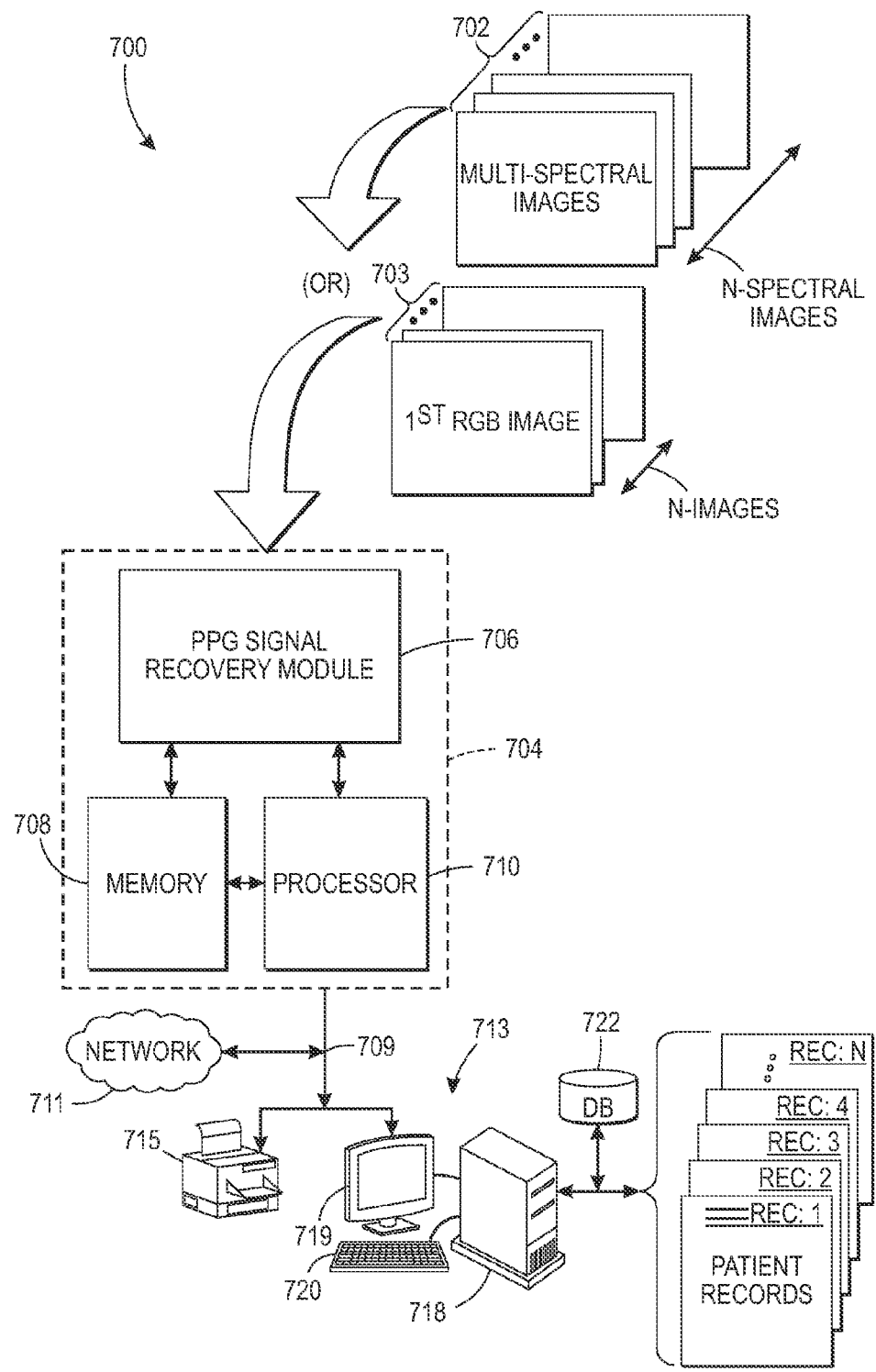
FIG. 7 illustrates a block diagram of one example signal processing system for performing various aspects of the present method.

Reference is now being made to FIG. 7 which illustrates a block diagram of one example processing system 700 for implementing various aspects of the present method described with respect to the flow diagrams of FIGS. 4-5.

The system of FIG. 7 receives a sequence of video images captured of a subject of interest intended to be monitored for cardiac function. The captured video images are either a plurality of multi-spectral images 702 captured using a multi-spectral video camera or a plurality of RGB images 703 capturing using a RGB video. The sequence of images 702 or 703 collectively comprises video data acquired over time.

Signal processing system 704 receives the video data into PPG signal recovery module 706 which performs all the functionality as described with respect to the flow diagrams of FIGS. 4-5. Memory 708 and CPU 710 facilitate the processing and output of the continuous PPG signal (at 709). The continuous PPG signal 709 is communicated to workstation 713 and print device 715 for further processing, viewing and/or for rendering. The continuous PPG signal may further be communicated to remote devices over network 711. Many aspects of network 711 are commonly known and a further discussion as to the construction and/or operation of a specific network configuration has been omitted. Suffice it to say, data is transmitted in packets between networked devices via a plurality of communication devices and links using established protocols. Data is transferred in the form of signals which may be, for example, electronic, electromagnetic, optical, light, or other signals. These signals are provided to a communications device such as a server which transmits and receives data packets by means of a wire, cable, fiber optic, phone line, cellular link, RF, satellite, or other medium or communications pathway.

Computer workstation 713 is shown comprising a computer case 718 housing a motherboard, CPU, memory, interface, storage device, and a communications link such as a network card. The computer workstation is also shown having a display device 719 such as a CRT, LCD, or touchscreen display, for display of the continuous PPG signal. An alphanumeric keyboard 720 and a mouse (not shown) effectuate a user input. It should be appreciated that the workstation has an operating system and other specialized software configured to display a variety of numeric values, text, scroll bars, pull-down menus with user selectable options, and the like, for entering, selecting, or modifying information displayed on the display device. Computer system 713 implements database 722 wherein various records are stored, manipulated, and retrieved in response to a query. Although the database is shown as an external device, the database may be internal to computer case 1018 mounted on a hard disk housed therein. A record refers to any data structure capable of containing information which can be indexed, stored, searched, and retrieved in response to a query. Patient information can be stored and/or retrieved to any of the records in database 722.

Any of the modules and processing units of FIG. 7 are in communication with workstation 713 via pathways (not shown) and may further be in communication with one or more remote devices over network 711. It should be appreciated that some or all of the functionality for any of the modules of the signal processing system 704 may be performed, in whole or in part, by components internal to workstation 713 or by a special purpose computer system. It should also be appreciated that various modules may designate one or more components which may, in turn, comprise software and/or hardware designed to perform the intended function. A plurality of modules may collectively perform a single function. Each module may have a specialized processor capable of executing machine readable program instructions. A module may comprise a single piece of hardware such as an ASIC, electronic circuit, or special purpose processor. A plurality of modules may be executed by either a single special purpose computer system or a plurality of special purpose computer systems in parallel. Connections between modules include both physical and logical connections. Modules may further include one or more software/hardware modules which may further comprise an operating system, drivers, device controllers, and other apparatuses some or all of which may be connected via a network.

One or more aspects of the present method may be implemented in conjunction with a smartphone such as an iPhone. In this embodiment, RGB and/or multi-spectral/hyperspectral video images are transmitted to a remote computer or server operating in a cloud environment wherein processing of the video data stream takes place in accordance with the teachings disclosed herein. The remote computing device, in turn, transmits the generated continuous PPG signal or results thereof such as, for instance, the existence or occurrence of cardiac arrhythmia to the smartphone for display. Such results may take the form of a text, video, or audio message that is displayed on the smartphone device. In another embodiment, all the computations (i.e., PPG signal recovery and the subsequent determination of the existence of cardiac arrhythmia) are performed within the smartphone with the results thereof displayed on the devices screen, communicated to a remote device via network 711, or sent to a pre-determined message recipient such as the subject's cardiac physician. Various aspects of the present method may be practiced in distributed computing environments where tasks are performed by a plurality of remote devices linked via network 711. Such embodiments are intended to fall within the scope of the appended claims.

Example Special Purpose Computer

Figure 8:
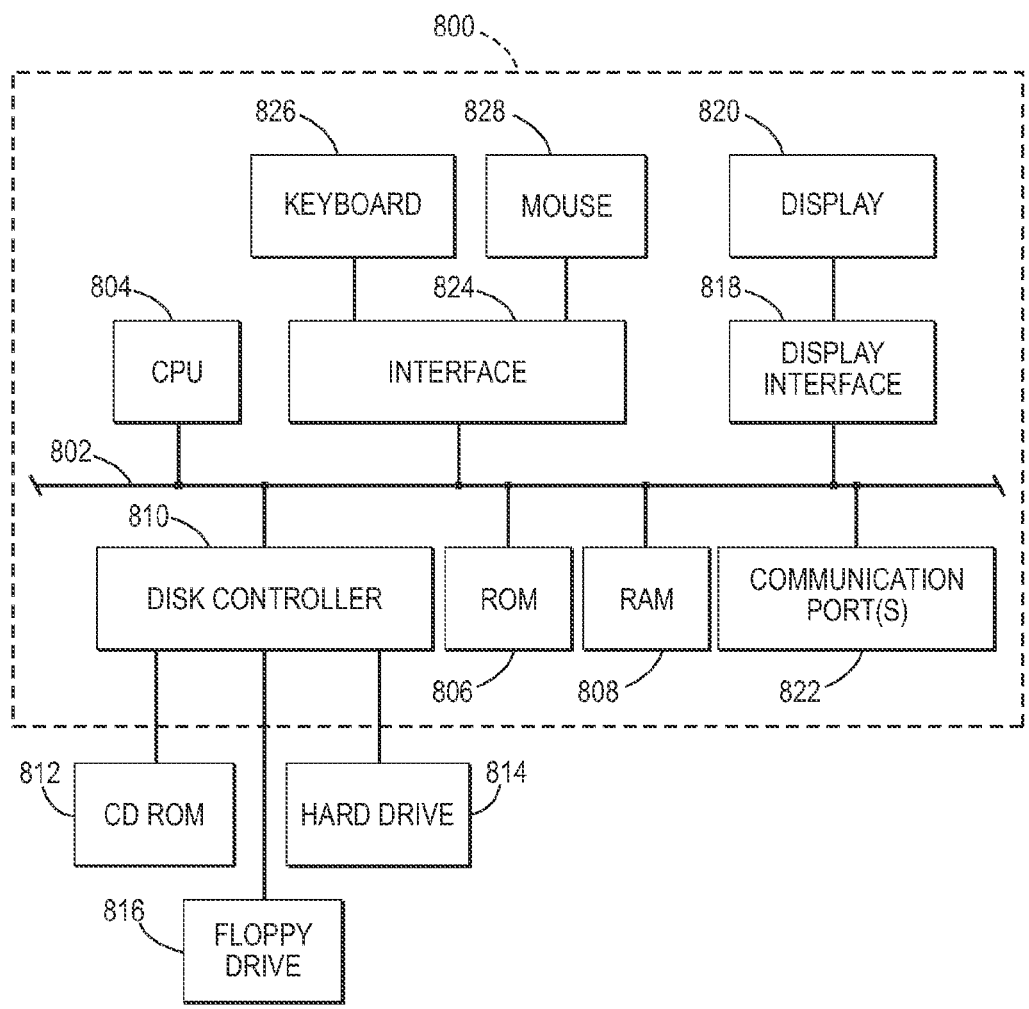
FIG. 8 illustrates a block diagram of one example special purpose computer for implementing one or more aspects of the present method as described with respect to the flow diagrams of FIGS. 4-5, and the block diagram of FIG. 7.

Reference is now being made to FIG. 8 which illustrates a block diagram of one example special purpose computer 800 for implementing one or more aspects of the present method as described with respect to the flow diagrams of FIGS. 4-5, and the block diagram of FIG. 7. Such a special purpose processor is capable of executing machine executable program instructions and may comprise any of a micro-processor, micro-controller, ASIC, electronic circuit, or any combination thereof.

In FIG. 8, communications bus 802 is in communication with a central processing unit (CPU) 804 capable of executing machine readable program instructions for performing any of the calculations, comparisons, logical operations, and other program instructions for performing any of the steps described above with respect to the flow diagrams and the block diagram hereof. Processor 804 is in communication with memory (ROM) 806 and memory (RAM) 808 which, collectively, constitute example storage devices. Such memory may be used to store machine readable program instructions and other program data and results to sufficient to carry out any of the functionality described herein. Disk controller 810 interfaces with one or more storage devices 814 which may comprise external memory, zip drives, flash memory, USB drives, or other devices such as CD-ROM drive 812 and floppy drive 816. Storage device stores machine executable program instructions for executing the methods hereof. Such storage devices may be used to implement a database wherein various records are stored. Display interface 818 effectuates the display of information on display 820 in various formats such as, for instance, audio, graphic, text, and the like. Interface 824 effectuates a communication via keyboard 826 and mouse 828, collectively a graphical user interface. Such a graphical user interface is useful for a user to enter information. Communication with external devices may occur using example communication port(s) 822. Such ports may be placed in communication with any of the example networks shown and described herein, such as the Internet or an intranet, either by direct (wired) link or wireless link. Example communication ports include modems, network cards such as an Ethernet card, routers, a PCMCIA slot and card, USB ports, and the like, capable of transferring data from one device to another. Software and data is transferred via the communication ports in the form of signals which may be any of digital, analog, electromagnetic, optical, infrared, or other signals capable of being transmitted and/or received by the communications interface. Such signals may be implemented using, for example, a wire, cable, fiber optic, phone line, cellular link, RF, or other signal transmission means presently known in the arts or which have been subsequently developed.

The teachings hereof can be implemented in hardware or software using any known or later developed systems, structures, devices, and/or software by those skilled in the applicable art without undue experimentation from the functional description provided herein with a general knowledge of the relevant arts. Furthermore, the teachings hereof may be partially or fully implemented in software using source code that can be used on a variety of computer platforms. One or more of the capabilities hereof can be emulated in a virtual environment or leverage off-the-shelf software.

One or more aspects of the methods described herein are intended to be incorporated in an article of manufacture, including one or more computer program products, having computer usable or machine readable media. The article of manufacture may be included on at least one storage device readable by a machine architecture embodying executable program instructions capable of performing the methodology described herein. The article of manufacture may be shipped, sold, leased, or otherwise provided separately either alone or as part of an add-on, update, upgrade, or product suite. It will be appreciated that various of the above-disclosed and other features and functions, or alternatives thereof, may be combined into other systems or applications. Presently unforeseen or unanticipated alternatives, modifications, variations, or improvements may become apparent and/or subsequently made by those skilled in the art which are also intended to be encompassed by the following claims. It will be appreciated that the above-disclosed and other features and functions, or alternatives thereof, may be desirably combined into many other different systems or applications. Changes to the above-described embodiments may be made without departing from the spirit and scope of the invention. The teachings of any printed publications including patents and patent applications, are each separately hereby incorporated by reference in their entirety.

What is claimed is:

1. A method for extracting a photoplethysmographic (PPG) signal on a continuous basis from a time-series signals obtained from video images captured of a subject being monitored for cardiac function in a non-contact remote sensing environment, the method comprising:

receiving, on a continuous basis, a time-series signal obtained from video images captured using a video imaging device of a region of exposed skin where a photoplethysmographic (PPG) signal of a subject of interest can be registered;

overlaying said received time-series signal with a sliding window, said sliding window defining segments of said received time-series signal for processing, each successive position of said sliding window defining a next segment of said time-series signal for processing;

defining a seed reference signal with a frequency range that approximates a frequency range of said subject's cardiac function; and processing segments of said received time-series signal by repeatedly:

performing constrained source separation (cICA) on said signal segment using said seed reference signal to obtain an estimated source signal, said cICA converging on an occurrence of one of: an error between said estimated source signal and said seed reference signal being less than a threshold, and a pre-defined number of iterations having occurred;

in response to said error being less than said threshold:

determining a frequency of said estimated source signal as said subject's estimated cardiac pulse rate for this time-series signal segment;

using said estimated source signal as said seed reference signal for processing a next time-series signal segment on a next iteration; and shifting said sliding window to define a next segment of said time-series signal, said next segment at least partially overlapping a previous time-series signal segment defined by said window on a last iteration.

2. The method of claim 1, wherein said video imaging device generates any combination of: NIR images, RGB images, RGB with NIR images, multispectral images, and hyperspectral video images.

3. The method of claim 1, wherein said time-series signal comprises one of: stored values, and values generated from a streaming video.

4. A system for extracting a photoplethysmographic (PPG) signal on a continuous basis from a time-series signals obtained from video images captured of a subject being monitored for cardiac function in a non-contact remote sensing environment, the system comprising:

a memory; and a processor in communication with said memory, said processor executing machine readable instructions for performing:

receiving, on a continuous basis, a time-series signal obtained from video images captured using a video imaging device of a region of exposed skin where a photoplethysmographic (PPG) signal of a subject of interest can be registered;

overlaying said received time-series signal with a sliding window, said sliding window defining segments of said received time-series signal for processing, each successive position of said sliding window defining a next segment of said time-series signal for processing;

defining a seed reference signal with a frequency range that approximates a frequency range of said subject's cardiac function; and processing segments of said received time-series signal by repeatedly:

performing constrained source separation (cICA) on said signal segment using said seed reference signal to obtain an estimated source signal, said cICA converging on an occurrence of one of: an error between said estimated source signal and said seed reference signal being less than a threshold, and a pre-defined number of iterations having occurred;
in response to said error being less than said threshold:
  determining a frequency of said estimated source signal as said subject's estimated cardiac pulse rate for this time-series signal segment;
  using said estimated source signal as said seed reference signal for processing a next time-series signal segment on a next iteration; and
  shifting said sliding window to define a next segment of said time-series signal, said next segment at least partially overlapping a previous time-series signal segment defined by said window on a last iteration.

5. The system of claim 4, wherein said time-series signal comprises one of: stored values, and values generated from a streaming video.

6. The method of claim 1, further comprising:
in response to said pre-defined number of iterations having occurred, performing one of:
  updating said seed reference signal by changing any of: a frequency, an amplitude, a phase, and a waveform of said seed reference signal, and using said updated reference signal as said seed reference signal to re-process said time-series signal segment; and
  selecting an estimated source signal obtained from having processed a previous time-series signal segment and using said selected estimated source signal as said seed reference signal to re-process said time-series signal segment.

7. The system of claim 4, wherein said video imaging device generates any combination of: NIR images, RGB images, RGB with NIR images, multispectral images, and hyperspectral video images.

8. The system of claim 4, further comprising:
in response to said pre-defined number of iterations having occurred, performing one of:
  updating said seed reference signal by changing any of: a frequency, an amplitude, a phase, and a waveform of said seed reference signal, and using said updated reference signal as said seed reference signal to re-process said time-series signal segment; and
  selecting an estimated source signal obtained from having processed a previous time-series signal segment and using said selected estimated source signal as said seed reference signal to re-process said time-series signal segment.

* * * * *